United States Patent
Barriskill et al.

(10) Patent No.: US 8,905,951 B2
(45) Date of Patent: Dec. 9, 2014

(54) MOTORIZED FUNCTIONAL ELECTRICAL STIMULATION STEP AND STAND TRAINER

(75) Inventors: Andrew Barriskill, Baltimore, MD (US); Scott Simcox, Baltimore, MD (US)

(73) Assignee: Restorative Therapies, Inc., Baltimore, MD (US)

(*) Notice: Subject to any disclaimer, the term of this patent is extended or adjusted under 35 U.S.C. 154(b) by 588 days.

(21) Appl. No.: 13/219,610

(22) Filed: Aug. 27, 2011

(65) Prior Publication Data

US 2013/0053734 A1    Feb. 28, 2013

(51) Int. Cl.

| | | |
|---|---|---|
| *A61H 1/02* | (2006.01) | |
| *A61N 1/36* | (2006.01) | |
| *A61N 1/04* | (2006.01) | |
| *A61H 23/02* | (2006.01) | |
| *A63B 69/00* | (2006.01) | |
| *A63B 21/005* | (2006.01) | |
| *A63B 22/06* | (2006.01) | |
| *A63B 71/00* | (2006.01) | |
| *A63B 21/00* | (2006.01) | |

(52) U.S. Cl.
CPC .......... *A61H 1/0229* (2013.01); *A61N 1/36003* (2013.01); *A61N 1/0452* (2013.01); *A61H 1/0262* (2013.01); *A61H 23/0254* (2013.01); *A61H 2201/1621* (2013.01); *A61H 2201/164* (2013.01); *A61H 2203/0406* (2013.01); *A61H 2230/805* (2013.01); *A63B 69/0064* (2013.01); *A63B 21/0058* (2013.01); *A63B 22/0664* (2013.01); *A63B 2022/067* (2013.01); *A63B 2071/0081* (2013.01); *A63B 2213/004* (2013.01); *A63B 21/00178* (2013.01); *A63B 2230/015* (2013.01)
USPC .......... 601/35; 601/5; 601/21; 601/33; 482/80

(58) Field of Classification Search
CPC ..... A61H 1/00; A61H 1/0214; A61H 1/0218; A61H 1/0262; A61H 1/0266; A61H 3/00; A61H 3/008; A61H 2001/00; A61H 2001/0237; A61H 2001/0266; A61H 2003/00; A61H 2201/1418; A61H 2201/164; A61H 2201/1652; A61H 2201/5007; A61H 2203/0406; A61H 2205/106; A61H 2205/12; A61H 2230/80; A61H 2230/805; A61H 1/0229; A61H 2201/1621; A61B 69/0064
USPC ............. 601/5, 23, 26, 27, 29, 31, 32, 33, 34, 601/35, 84, 86, 87, 90, 93, 97, 98, 101, 104, 601/21; 482/52, 54, 57, 66, 69, 70, 79, 80
See application file for complete search history.

(56) References Cited

U.S. PATENT DOCUMENTS 2,109,188 A * 2/1938 Bajanova ..................... 601/34
3,917,261 A * 11/1975 Small et al. .................. 601/29
(Continued)

OTHER PUBLICATIONS

Behrman, Andrea L. and Harkema, Susan J., Locomotor Training After Human Spinal Cord Injury: A Series of Case Studies, Phys. Ther. 80:688-700 (2000).

(Continued)

*Primary Examiner* — Quang D Thanh
(74) *Attorney, Agent, or Firm* — Whiteford, Taylor & Preston, LLP; Joseph L. Morales

(57) ABSTRACT

A functional electrical stimulation step and stand system comprising two footplates (left and right) connected to a primary drive motor that cause the footplates to move in a reciprocal motion. The footplates are further connected to corresponding servos, which allow for control of the movement of the footplate with respect to an axis. system comprises an electrical stimulation control unit. The stimulation step and stand system further comprises a control unit that has electrical stimulation leads connected to electrodes that deliver an electrical impulse to a patient's muscles. In a further embodiment, the control unit has one or more wireless stimulators.

10 Claims, 8 Drawing Sheets

(56) References Cited

U.S. PATENT DOCUMENTS

| | | | |
|---|---|---|---|
| 2005/0251067 A1* | 11/2005 | Terry | 601/5 |
| 2010/0248903 A1* | 9/2010 | Cardile | 482/51 |
| 2010/0262048 A1* | 10/2010 | Shinomiya et al. | 601/35 |

OTHER PUBLICATIONS

Belanger, Marc et al., Electrical Stimulation: Can It Increase Muscle Strength and Reverse Osteopenia in Spinal Cord Injured Individuals?, Arch. Med. Rehabil. 81:1090-1098 (2000).

Colombo, Gery et al., Treadmill Training of Paraplegic Patients Using a Robothic Orthosis, J. Rehabil. Research and Dev. 37(6):693-700 (2000).

Daly, Janis J. et al., Therapeutic Neural Effects of Electrical Stimulation, IEEE Transactions on Rehabil. Eng. 4 (4):218-230 (1996).

Dietz, V. et al., Locomotor Capacity of Spinal Cord in Paraplegic Patients, Ann. Neurol. 37:574-582 (1995).

Dobkin, B. et al., Weight-Supported Treadmill vs. Overground Training for Walking after Acute Incomplete SCI, Neurology 66:484-493 (2006).

Pouran, Faghri D. et al., Functional Electrical Stimulation Leg Cycle Ergometer Exercise: Training Effect on Cardiorespiratory Responses of Spinal Cord Injury Subjects at Rest and During Submaximal Exercise, Arch. Phys. Med. Rehabil. 73:1085-93 (1992).

Field-Foote, Edelle C., et al., Locomotor Training Approaches for Individuals with Spinal Cord injury: A Preliminary Report of Walking-related Outcomes, J. Neurol. Phys. Therapy 29(3):127-137 (2005).

Frotzler, Angela et al., Effect of Detraining on Bone and Muscle Tissue in Subjects with Chronic Spinal Cord Injury After a Period of Electrically-Stimulated Cycling: A Small Cohort Study, J. Rehabil. Med. 41:282-285 (2009).

Griffin, L. et al., Functional Electrical Stimulation Cycling Improves Body Composition, Metabolic and Neural Factors in Persons with Spinal Cord Injury, J. Electromyog. Kinesiol. (2008).

Hesse, Stefan and Uhlenbrock, Dietmar, A Mechanized Gait Trainer for Restoration of Gait, J. Rehabil. Res. and Dev. 37(6):701-708 (2000).

Kinikou, Maria and Conway, Bernard, Reflex Effects of Induced Muscle Contraction in Normal and Spinal Cord Injured Subjects, Muscle & Nerve (2002).

McDonald, John W., et al., Late Recovery Following Spinal Cord Injury, J. Neurosurg 97:252-265 (2002).

Mohr, Thomas, et al., Long Term Adaptation to Electrically Induced Cycle Training Severe Spinal Cord Injured Individuals, Spinal Cord 35:1-16(1997).

Shields, Richard K. and Dudley-Javorski, Shauna, Musculoskeletal Plasticity After Acute Spinal Cord Injury: Effects of Long-Term Neuromuscular Electrical Stimulation Training, J. Neurophysiology 95:2380-2390 (2006).

Wernig, A and Muller, S, Laufband Locomotion with Body Weight Support Improved Walking in Persons with Severe Spinal Cord Injuries, Paraplegia 30:229-238 (1992).

Wirz, Markus, et al., Effectiveness of Automated Locomotor Training in Patients with Chronic Incomplete Spinal Cord Injury: A Multicenter Trial, Arch. Phys. Med. Rehabil. 86:672-80 (2005).

\* cited by examiner

MOTORIZED FUNCTIONAL ELECTRICAL STIMULATION STEP AND STAND TRAINER

FIELD OF THE INVENTION

This invention relates to a training device for rehabilitation of individuals suffering from neurological injuries. More particularly, the present invention relates to a device that utilizes both mechanical and electrical stimulation of individual's muscles.

DESCRIPTION OF THE BACKGROUND

The recovery of walking is one of the main goals of patients after a neurological impairment (including stroke, multiple sclerosis, cerebral palsy and spinal cord injury (SCI)) as limitations in mobility can adversely affect most activities of daily living. Following a neurological injury, there is often impaired control of balance, paralysis, or weakness of lower extremity muscles including commonly those that activate the ankle. This often has a substantial adverse impact on walking. Specifically, individuals may suffer difficulties supporting their body weight during the stance phase, or shifting weight during the transition to swing, or lifting their foot for toe clearance during the swing phase due to the weakness associated with the injury. Gait training can be done
i. with therapist-assisted over ground ambulation (with or without assistive device)
ii. in a Body Weight Supported Treadmill Training (BWSTT) environment, where assistance for the movement of legs and the pelvis is provided manually by a therapist or
iii. by a robotic device (Lokomat, Auto-Ambulator or Gait Trainer), or in water (weight supported environment, with or without a treadmill).

Over ground gait training (with or without a Functional Electrical Stimulation (FES) orthosis) can only be used for individuals with already able to support body weight in an upright position.

BWSTT, robotic device gait training and aquatherapy gait training (training in water) can potentially be used to enhance loco-motor abilities in neurologically impaired individuals, as lack of trunk balance and ability to bear weight in an upright position are replaced by the supporting abilities of the device or environment used (harness, exoskeleton or water). But they are not typically used in clinical practice to aid in locomotor training in individuals with motor complete impairments as this training would need specialized, center based, expensive environment (i.e. therapeutic pool, robotic exoskeleton) or is very labor intensive (sometimes requiring 2-3 therapists' sustained effort over long periods of time).

BWSTT with manual or robotic assistance of the legs and the pelvis has been used as a promising rehabilitation method designed to improve motor function and ambulation in people with SCI (Behrman and Harkema 2000; Dietz et al. 1995; Wernig and Muller 1992; Wirz et al. 2005; Dobkin et al. 2006; Field-Fote et al. 2005). However, while BWSTT has been shown to provide improvements in locomotor ability, motor function, and balance for some patients, the current technology used to assist with the training is typically very expensive, requires trained therapists for utilization and can only be used in a rehabilitation center. Several robotic BWSTT systems have been developed for automating locomotor training, including the Lokomat (Colombo et al. 2000) and Gait Trainer (GT) (Hesse and Uhlenbrock 2000).

The Lokomat is a motorized exoskeleton that drives hip and knee motion with fixed trajectory using four DC motors (Colombo et al. 2000). One limitation is that it is difficult to back drive the Lokomat because it uses high advantage, ball screw actuator. The GT rigidly drives the patient's feet through a stepping motion using a crank-and-rocker mechanism attached to foot platforms (Hesse and Uhlenbrock 2000). These robotic systems have their basic design goal to assist patients in producing correctly shaped and timed locomotor movements. This approach is effective in reducing therapist labor in locomotor training and increasing the total duration of training, but shows relatively limited functional gains for some patients (Wirz et al. 2005; Field-Fote et al. 2005). For instance, only 0.11 m/s gait speed improvement is obtained following prolonged training using the Lokomat (Wirz et al. 2005).

FES has been previously used to enhance the quality of gait training whether as an assistive device (FES orthosis for foot drop) or to enhance muscle strength and improve cardiovascular resistance (FES ergometer), thus decreasing gait induced fatigue. FES has also been used extensively in the rehabilitation of individuals with SCI to:
i. improve muscle mass and strength (Frotzler A, Coupaud S, Perret C, Kakebeeke T H, Hunt K J, Eser P. Effect of detraining on bone and muscle tissue in subjects with chronic spinal cord injury after a period of electrically-stimulated cycling: a small cohort study. Swiss Paraplegic Research, Nottwil, Switzerland; Thomas Mohr, Jesper L Andersen, Fin Biering-Sùrensen, Henrik Galbo, Jens Bangsbo, Aase Wagner and Michael Kjaer. Long term adaptation to electrically induced cycle training in severe spinal cord injured individuals. Spinal Cord (1997) 35, 1±16)
ii. control spasticity (Maria Knikou, PhD, and Bernard A. Conway, PhD. Reflex Effects Of Induced Muscle Contraction In Normal And Spinal Cord Injured Subjects. Muscle Nerve 26: 374-382, 2002; Daly J., et al. Therapeutic neural effects of electrical stimulation. IEEE Trans Rehabil Eng 4:218-230, 1996; Robinson C. J., et al. Spasticity in Spinal-Cord Injured Patients 0.1. Short-Term Effects of Surface Electrical-Stimulation. Arch Phys Med Rehab 69:598-604, 1988)
iii. improve cardiovascular endurance and respiratory function (Puran D Faghri, Roger M Glaser, Stephen F Figoni. Functional Electrical Stimulation Leg Cycle Ergometer Exercise: Training Effects on Carriorespiratory Responses of Spinal Cord Injured Subjects at Rest and During Submaximal Exercise. Arch Phys Med Rehabil 73:1085-1093)
iv improve bone mass (Belanger M, Stein R B, Wheeler G D, Gordon T, Leduc B. Electrical stimulation: can it increase muscle strength and reverse osteopenia in spinal cord injured individuals? Arch Phys Med Rehabil 2000; 81(8):1090-1098; McDonald J W, Becker D, Sadowsky C L, Jane J A, Sr., Conturo T E, Schultz L M. Late recovery following spinal cord injury. Case report and review of the literature. J Neurosurg 2002; 97(2 Suppl):252-265) and
v. improve body composition (L. Griffin, M. J. Decker, J. Y. Hwang, B. Wang, K. Kitchen, Z. Ding, J. L. Ivy. Functional electrical stimulation cycling improves body composition, metabolic and neural factors in persons with spinal cord injury. J Electromyography and Kinesiol 2008: 1-8).

FES has been postulated to even alter neuronal control, altering central nervous system plasticity and improving functional tasks performance (Richard K. Shields and Shauna Dudley-Javoroski. Musculoskeletal Plasticity After Acute Spinal Cord Injury: Effects of Long-Term Neuromuscular Electrical Stimulation Training J Neurophysiol 95: 2380-2390, 2006).

Combining gait training with FES activation of selected muscles involved in stepping has been already achieved and there are several commercially available FES driven orthosis for utilization in individuals with SCI, mainly to correct foot drop (Bioness L300, Walk Aid). In addition, in clinical practice, therapists are frequently utilizing hand held triggered neuromuscular electrically stimulated (NMES) devices to aid in foot/toe clearing during the swing phase of the gait when working with individuals with neurologic lower limb weakness.

SUMMARY OF THE INVENTION

One object of the present invention is to provide a functional electrical stimulation step and stand system comprising two footplates (left and right) connected to a primary drive motor that cause the footplates to move in a reciprocal motion. The footplates are further connected to corresponding servos, which allow for control of the movement of the footplate with respect to an axis. The ability to control the movement of the footplate is defined as the firmness of the footplate.

In a further object of the present invention, the system comprises an control unit that manages a computer and a six channel stimulator. The control unit has electrical stimulation leads that connect to electrodes that deliver an electrical impulse to a patient's muscles. In a further embodiment, the control unit has one or more wireless stimulators.

BRIEF DESCRIPTION OF THE DRAWINGS

The above and other features, aspects, and advantages of the present invention are considered in more detail, in relation to the following description of embodiments thereof shown in the accompanying drawings, in which.

DETAILED DESCRIPTION

The invention summarized above may be better understood by referring to the following description, the accompanying drawings, and the claims listed below. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
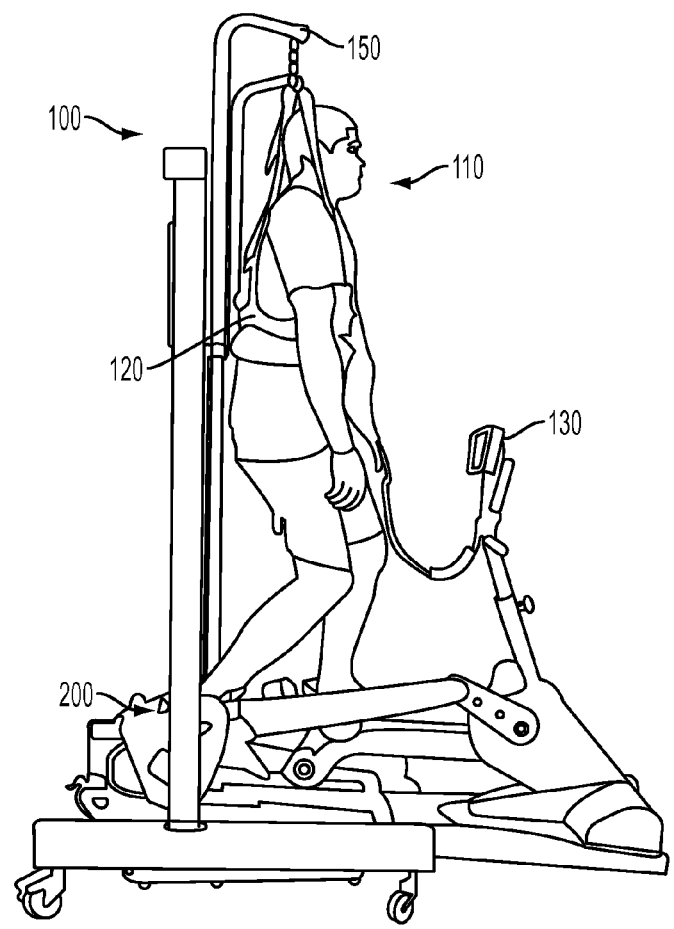
FIG. 1 is a picture of a device in accordance with one embodiment of the invention.

As shown in FIG. 1, one embodiment of the invention is a trainer 100 that combines a robotic device that simulates stepping and standing with FES while the individual 110 is safely supported in a harness 120. This design has the potential to tap into neuro-plasticity driven loco-motor patterning while increasing muscle strength and cardiovascular endurance and be safely applied in a center or home-based environment.

Figure 2:
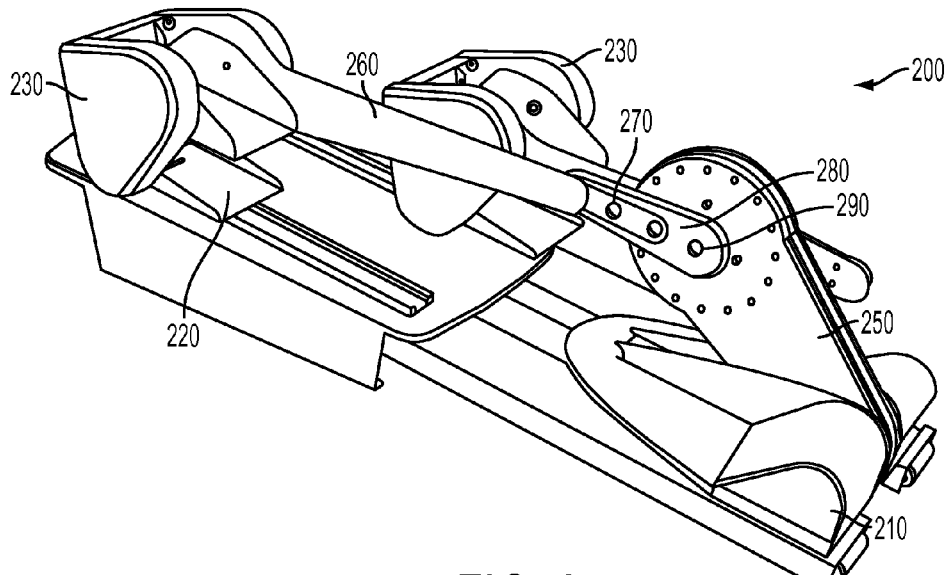
FIG. 2 is a graphical representation of a stepper assembly in accordance with one embodiment of the present invention.

The motion of the individual's feet is controlled by a foot assembly 200 as shown in FIG. 2. The foot assembly 200 (also referred to as the stepper assembly) incorporates three motors. The primary drive motor 210 provides for transverse motion of foot plates 220 while a servo 230 built into both the left and right footplate 220 allow the software to independently control the motion of the foot about the ankle in the sagittal plane. This control can either assist the foot movement being evoked volitionally or electrically or it can resist such movement.

In one further embodiment of the present invention, a stand training mode allows the foot plates to be brought together helping the individual patient to develop standing skills utilizing a combination of electrically evoked peripheral muscle contractions or volitional and or electrically evoked centrally driven muscle contractions. In this mode the footplate servos 230 can be used to induce perturbations, which the individual can train to counteract.

The motors controlling each footplate 220 can also be commanded to produce a vibration motion of the footplates in the sagittal plane either during standing or stepping motions. This vibration can be used to deliver therapeutic benefits including the reduction of spasticity. FES driven gait training utilizing the training device 100 will be safe for both motor complete and incomplete neurologically impaired individuals. In addition, the training device 100 can increase the walking abilities of individuals with many types of neurological impairments. Given this the training device 100 can be safely used in a home based environment to perform long term gait training in individuals with varying degrees of neurological related paralysis.

Figure 3:
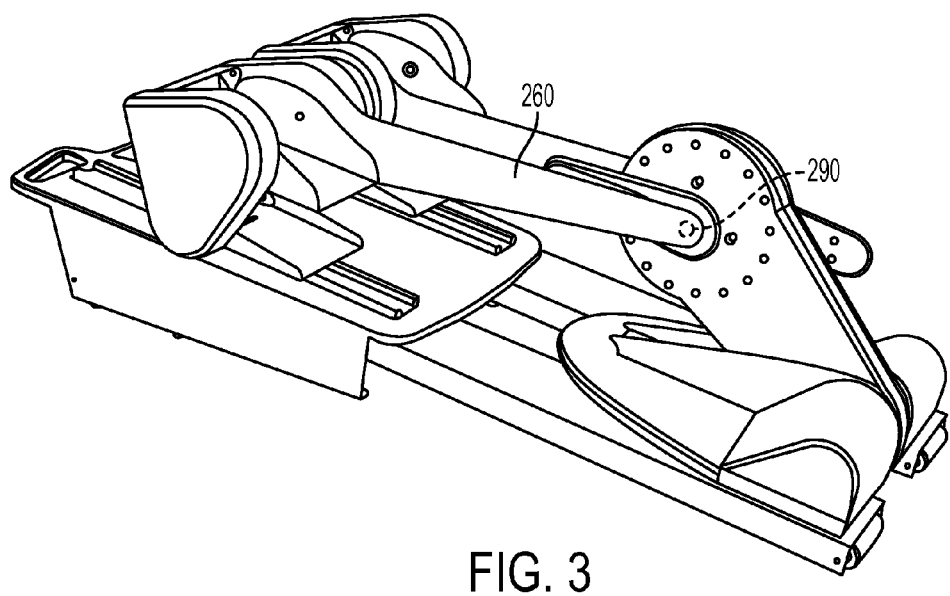
FIG. 3 is a graphical representation of the stepper assembly in the standing position.

As shown in FIG. 1, training device 100 is composed of a stepper assembly 200, a control unit 130, and a patient hoist 150 and harness 120. The stepper assembly 200, as shown in FIG. 2, has a drive motor 210 connected to the drive assembly 250. The drive assembly 250 is connected to the foot plates 220 by cranks 260 (left and right respectively) through a drive arm 280. The cranks 220 are connected to the drive arm 280 at different positions 270 and held in place by a magnet. The positions 270 determine the step lengths for the foot plates 220. In one particular embodiment, the drive arm 280 has three positions 270 resulting in 18", 15", and 12" steps. An additional position 290 brings the footplates 220 together proving a standing position to the individual, as shown in FIG. 3.

Figure 4:
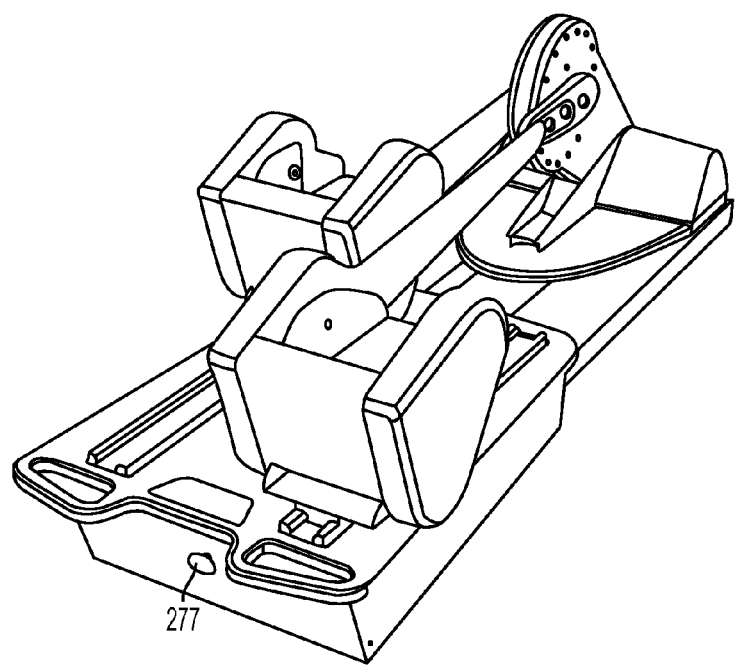
FIG. 4 is a perspective view of the stepper assembly.
Figure 5:
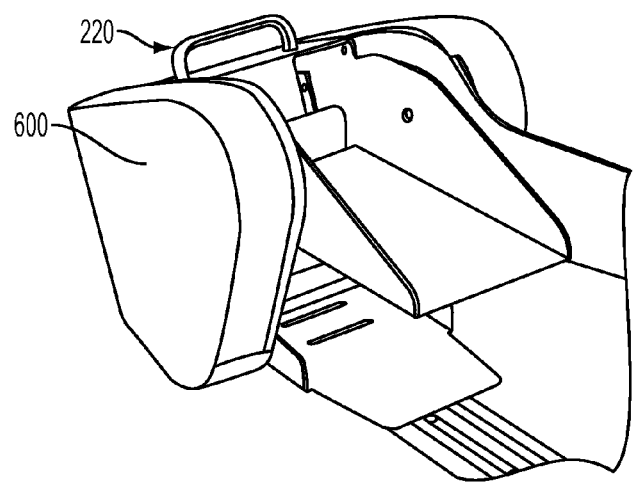
FIG. 5 is a detailed view of the foot plate.
Figure 6:
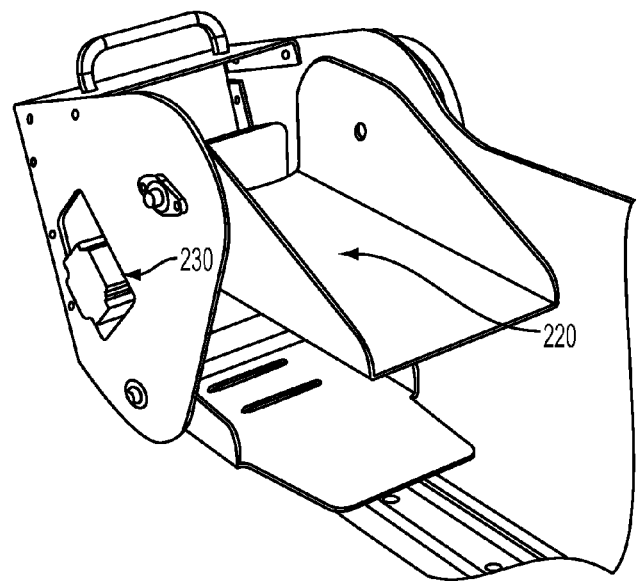
FIG. 6 is a detailed view of the foot plate with the servo plate removed.
Figure 7:
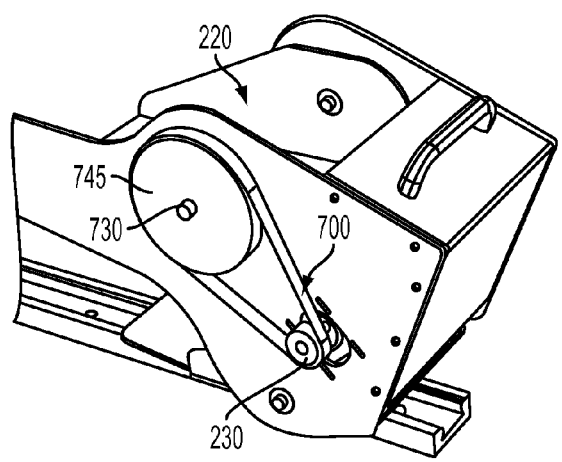
FIG. 7 is a detailed view of the foot plate showing the servo drive belt.

As shown in FIG. 4, the stepper assembly 200 further comprises an emergency stop 277 that allows a technician to stop the drive assembly 250 from moving the foot plates 220. FIG. 5 shows a close up view of the right side foot plate 220 and servo 230. In FIG. 6, the servo cover 600 has been removed and the servo 230 is shown. FIG. 7 shows a view of the footplate from the opposite side than that shown in FIG. 6. The servo 230 motor connects to a drive belt 700 that controls the foot plate 220. The servo 230 connects to a pulley 745 through the drive belt 700. When the servo motor actuates the belt 700, the pulley 745 turns around the axis 730 causing the footplate to rotate about the axis 730. Left unpowered, each footplate moves through a range of plantar and dorsi flexion movement that is a natural product of the transverse motion.

Figure 8:
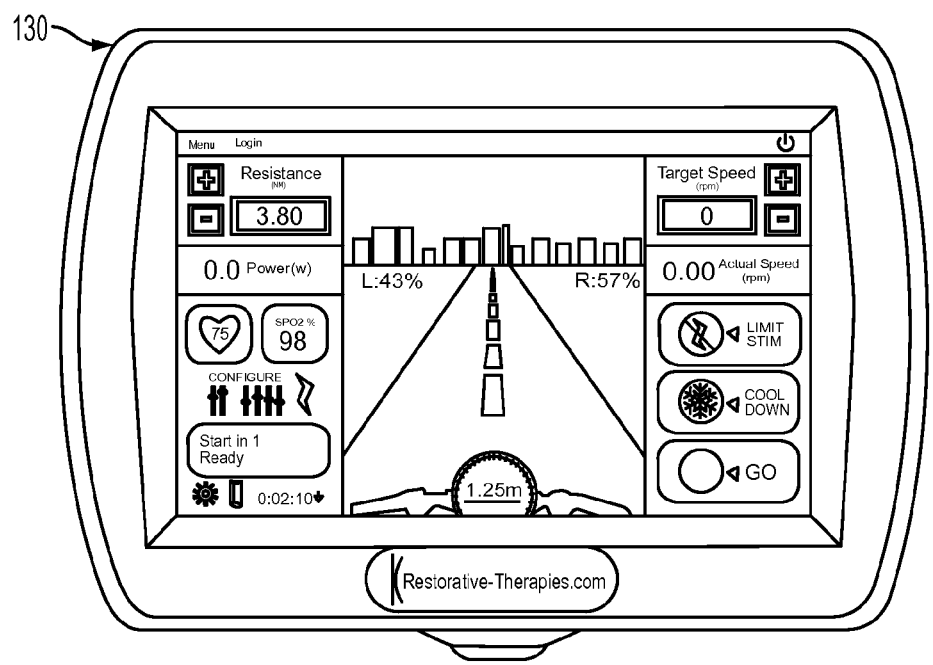
FIG. 8 is a graphical representation of the control unit.
Figure 9:
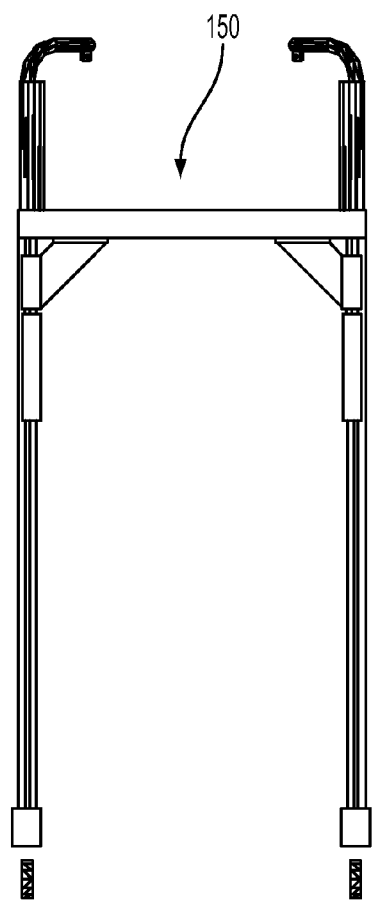
FIG. 9 is a front view of the patient hoist.
Figure 10:
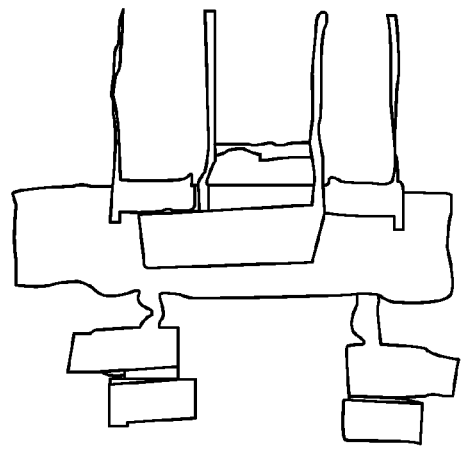
FIG. 10 is a front view of the harness.

In one particular embodiment, the trainer 100 has a control unit 130, as shown in FIG. 8, which includes a computer and a 6 channel stimulator. The stimulator produces the functional electrical stimulation to evoke muscle contractions. The computer controls the operation of the stimulator, the drive motor 210 and the two footplate servos 230. Software controlling the servo motors which power the left and right footplates can be used to guide a patient's foot through a normal range of motion in the sagittal plane during stepping training.

Figure 11:
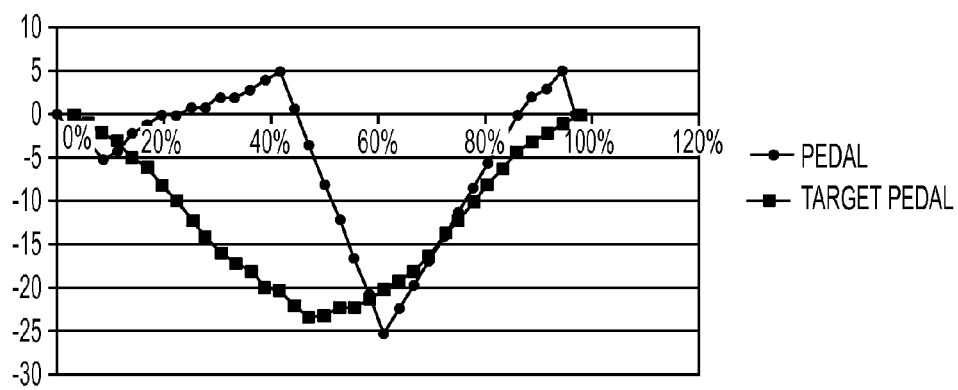
FIG. 11 is a graph showing the displacement of the pedals with and without servo input.

When in use, the trainer 100 can be utilized to track the appropriate travel of the individual's feet. FIG. 11 is a graph that shows how the footplate pedal moves with respect to gravity when unpowered (pedal trace) compared with how the ankle of an able bodied individual moves when stepping (target pedal trace) vs. percentage of phase of the gait cycle.

Figure 12:
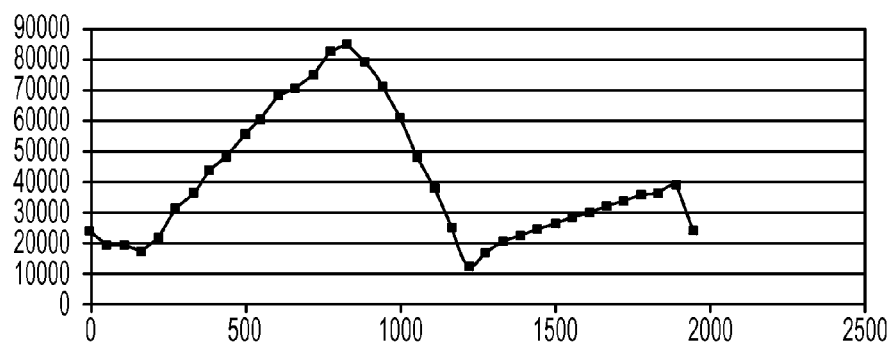
FIG. 12 is a graph that shows the various positions of the servo can be commanded.
Figure 13:
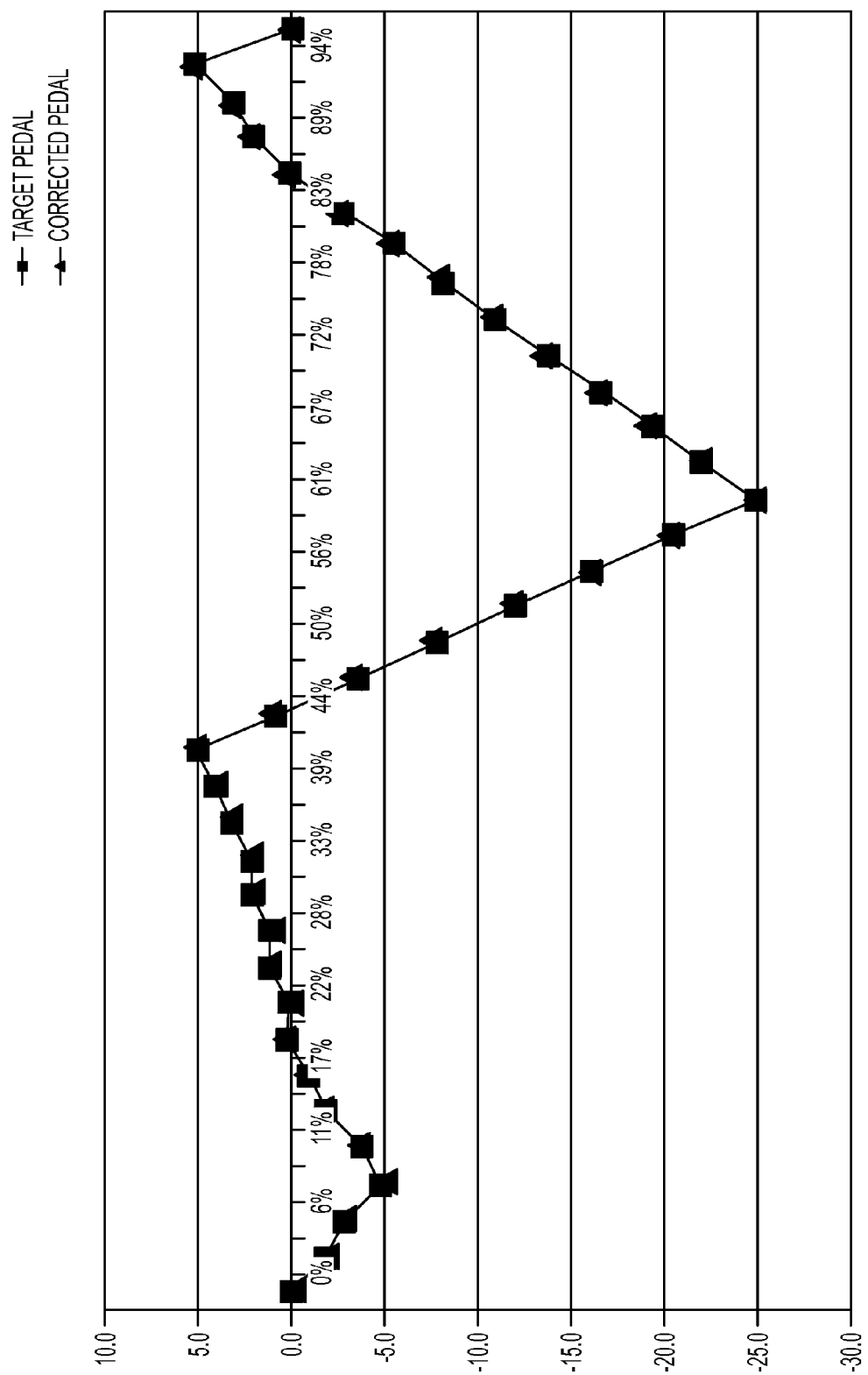
FIG. 13 is a graph that shows the result of commanding the servo to move the foot plate for a normal gait.

Furthermore, in FIG. 12 shows one way in which a footplate servo motor may be commanded to make the footplate's position coincident with normal gait. For example, commanding the motor to move 2452 positions results in a 1 degree movement path of the footplate. Superimposing this motor driven footplate movement with the unpowered footplate movement that arises from the transverse motion brings the footplate motion (corrected pedal trace) coincident with the ankle movement of normal gait (target pedal trace) vs. percent of the gait cycle as shown in FIG. 13.

Producing this normal ankle movement on this trainer 100 is one of the possible uses of the footplate servo motors. In one exemplary embodiment, the motors are also be used to produce vibration while standing or an exaggerated ankle motion for motor skill relearning purposes or a reduced ankle motion to accommodate patients with reduced range of motion in one or both ankle joints. In one exemplary embodiment, software varies the current supplied to each footplate servo which has the effect of varying the firmness of the footplate. Footplate firmness can be varied during a therapy session for example to gradually overcome plantar flexion muscle tone.

In one embodiment of the present invention, the control unit 130 provides up to 10 channels of electrical. It is contemplated that any number of channels may be utilized to provide electrical stimulation. In one alternative embodiment, the control unit 130 further includes a 6 channel electrical stimulator and a BlueTooth communications link that allows it to control up to four additional single channel stimulators.

The muscle groups to be stimulated are selected based upon how the patient presents. For example a hemiparetic patient may only require muscles on one side to be electrically stimulated.

Our invention allows the following muscle groups to be selected for electrical stimulation each either bilaterally or unilaterally:

Gluteals
Quadriceps
Hamstrings
Gastrocnemius
Anterior tibialis
Erector spinae
Abdominals The electrical stimulation is delivered to each muscle group via adhesive skin surface electrodes at the appropriate time in the gait cycle as determined by the position of drive arms in their circular path.

A further embodiment of the invention allows the electrical stimulation angles to be adjusted. The following is a table of default angles that can be provided in one particular embodiment of the present invention. The 0 degree position is the left drive arm at top dead center.

| Muscle group | Stimulation on angle | Stimulation off angle |
| --- | --- | --- |
| Left quadriceps | 50 | 285 |
| Right quadriceps | 230 | 105 |
| Left hamstring | 235 | 70 |
| Right hamstring | 55 | 250 |
| Left gluteal | 90 | 245 |
| Right gluteal | 270 | 65 |
| Left gastroc | 235 | 70 |
| Right gastroc | 55 | 250 |
| Left anterior tibialis | 50 | 285 |
| Right tibialis | 230 | 105 |
| Left abdominal | 340 | 180 |
| Right abdominal | 160 | 359 |
| Left erector spinae | 190 | 290 |
| Right erector spinae | 10 | 110 |

The invention has been described with references to a preferred embodiment. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

The invention claimed is:

1. A functional electrical stimulation step and stand system, comprising:
   a left footplate and a right footplate, wherein both left and right footplates are connected to a primary drive motor that causes the footplates to move in a reciprocal motion;
   said left footplate further connected to a left servo motor and said right footplate connected to a right servo motor, wherein each of said right and left servo motors causes its respective footplate to rotate about an axis;
   a control unit connected to the left and right servo motors and which controls the actuation of the left and right servo motors, wherein the control unit further comprises functional electrical stimulation leads attached to skin adhesive electrodes and wherein said adhesive electrodes deliver electrical stimulation to a patient's muscles; and
   a hoist capable of connecting to a harness and holding the patient in an upright position when in use.

2. The functional electrical stimulation step and stand system recited in claim 1, further comprising two drive arms connecting said primary drive motor to each of said left and right footplates, wherein said drive arms comprise various attachment points for connecting to corresponding right and left cranks at different attachment positions.

3. The functional electrical stimulation step and stand system recited in claim 2, wherein the footplates are attached to the drive arms by the corresponding left and a right cranks.

4. The functional electrical stimulation step and stand system recited in claim 2, wherein attachment of said drive arms at one of said attachment positions results in a step length based on the attachment point.

5. The functional electrical stimulation step and stand system recited in claim 4, wherein one of the attachment positions results in the footplates being parallel to each other facilitating the patient's standing position.

6. The functional electrical stimulation step and stand system recited in claim 1, wherein the footplate servo motors are configured to cause their respective footplate to vibrate.

7. The functional electrical stimulation step and stand system recited in claim 1, wherein the control unit is configured to assists foot movement being evoked volitionally or electrically.

8. The functional electrical stimulation step and stand system recited in claim 1, wherein the control unit further comprises an additional one or more wireless single channel stimulators.

9. The functional electrical stimulation step and stand system recited in claim 1, wherein the control unit is configured to resist foot movement.

10. The functional electrical stimulation step and stand system recited in claim 1, wherein the control unit further comprises up to ten single channel stimulators.

* * * * *